(12) United States Patent
Okude et al.

(10) Patent No.: US 12,309,945 B2
(45) Date of Patent: May 20, 2025

(54) BIOLOGICAL DEVICE

(71) Applicant: Murata Manufacturing Co., Ltd., Nagaokakyo (JP)

(72) Inventors: Kyoshiro Okude, Nagaokakyo (JP); Genta Nakano, Nagaokakyo (JP); Kota Tsubakizaka, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 202 days.

(21) Appl. No.: 18/328,529

(22) Filed: Jun. 2, 2023

(65) Prior Publication Data
US 2023/0413460 A1 Dec. 21, 2023

(30) Foreign Application Priority Data

Jun. 20, 2022 (JP) .................................. 2022-099118

(51) Int. Cl.
| | |
|---|---|
| *G06F 1/16* | (2006.01) |
| *A61B 5/00* | (2006.01) |
| *B01D 39/16* | (2006.01) |
| *H05K 5/00* | (2025.01) |
| *H05K 5/02* | (2006.01) |
| *H05K 7/00* | (2006.01) |
| *A61B 5/01* | (2006.01) |

(52) U.S. Cl.
CPC ......... *H05K 5/0215* (2022.08); *A61B 5/6801* (2013.01); *B01D 39/16* (2013.01); *H05K 5/0086* (2013.01); *A61B 5/01* (2013.01)

(58) Field of Classification Search
CPC .. H05K 5/0215; H05K 5/0086; H05K 5/0216; H05K 5/0214; H05K 5/0213; A61B 5/6801; A61B 5/01; A61B 5/6802; A61B 5/6813; A61B 5/683; A61B 5/6846; A61B 5/68; B01D 39/16; B01D 39/14
See application file for complete search history.

(56) References Cited

U.S. PATENT DOCUMENTS

| | | | | |
|---|---|---|---|---|
| 9,281,538 | B2 * | 3/2016 | Ueda | H01M 10/425 |
| 2005/0229560 | A1 * | 10/2005 | Eder | B01D 46/0016 |
| | | | | 55/467 |
| 2009/0192366 | A1 * | 7/2009 | Mensinger | G16H 40/63 |
| | | | | 706/14 |
| 2009/0192745 | A1 * | 7/2009 | Kamath | A61B 5/14532 |
| | | | | 702/85 |

(Continued)

FOREIGN PATENT DOCUMENTS

| | | |
|---|---|---|
| JP | 2019-063230 A | 4/2019 |
| WO | 2019065029 A1 | 4/2019 |

*Primary Examiner* — Anthony M Haughton
(74) *Attorney, Agent, or Firm* — ArentFox Schiff LLP

(57) ABSTRACT

A biological device that includes a case, an electronic unit, a gas-liquid separator, and an insulating sheet. The case is wearable on a body. The electronic unit is in an internal space of the case. The gas-liquid separator is attached to the case. The insulating sheet is attached to the case. The case has a communicating hole that connects the internal space and an external space of the case along a first direction. The gas-liquid separator and the insulating sheet are disposed apart from each other in the first direction. The gas-liquid separator, the electronic unit, and the insulating sheet overlap each other in a plan view of the biological device in the first direction.

14 Claims, 3 Drawing Sheets

(56) References Cited

U.S. PATENT DOCUMENTS

| | | | |
|---|---|---|---|
| 2018/0078778 A1* | 3/2018 | Ternes | A61N 1/37 |
| 2019/0000350 A1* | 1/2019 | Narayan | G16H 50/50 |
| 2020/0323452 A1* | 10/2020 | Mahajan | A61B 5/0022 |
| 2020/0373527 A1 | 11/2020 | Furutani et al. | |
| 2022/0101760 A1* | 3/2022 | Lee | G09F 9/301 |

* cited by examiner

BIOLOGICAL DEVICE

CROSS REFERENCE TO RELATED APPLICATIONS

The present application claims priority to Japanese Patent Application No. 2022-099118, filed Jun. 20, 2022, the entire contents of which are incorporated herein by reference.

BACKGROUND OF THE INVENTION

Field of the Invention

The present invention relates to a biological device.

Description of the Related Art

International Publication No. 2019/065029 describes a biological device that is worn on a body. The biological device includes a case, an electronic unit, and a gas-liquid separation sheet. The case has a communicating hole that connects the internal space of the case and the external space of the case to each other. The electronic unit is built into the case. The electronic unit includes electronic circuits, a power supply, and electronic boards. The gas-liquid separation sheet blocks the communicating hole of the case. The gas-liquid separation sheet is pervious to gas and impervious to liquid water.

SUMMARY OF THE INVENTION

The biological device described in International Publication No. 2019/065029 can prevent intrusion of water into the case but does not specifically consider the insulation inside and outside the case. In the event that a discharging device, such as a cautery knife or a defibrillator, is used near a portion of the body of a user on which the biological device is worn, the discharging device may apply an electric impact to the biological device. Accordingly, an electric current may flow from the outside of the case of the biological device to the electronic unit built into the case of the biological device.

To solve the problem described above, according to an aspect of the present disclosure, there is provided a biological device, the biological device including: a case defining an internal space and having a communicating hole connecting the internal space and an external space of the case to each other along a first direction, the case being constructed to be wearable on a body; an electronic unit in the internal space of the case; a gas-liquid separator attached to the case and blocking the communication hole; and an insulating sheet attached to the case or the electronic unit and disposed apart from the gas-liquid separator in the first direction, wherein the gas-liquid separator, the electronic unit, and the insulating sheet overlap the communicating hole in a plan view of the biological device in the first direction.

In the structure described above, the gas-liquid separator, the electronic unit, and the insulating sheet overlap the communicating hole in the plan view in the first direction. Accordingly, the insulating sheet can prevent an electric current from flowing from the outside of the case to the electronic unit through the communicating hole.

To solve the problem described above, according to another aspect of the present disclosure, there is provided a biological device including: a case wearable on a body; a gas-liquid separator constituting part of a wall of the case, the gas-liquid separator forming a path allowing gas to pass between an internal space within the case and an external space of the wall in a first direction, the first direction being a thickness direction of the wall; an electronic unit in the case; and an insulating sheet attached to the case or the electronic unit and disposed apart from the gas-liquid separator in the first direction, wherein the gas-liquid separator, the electronic unit, and the insulating sheet overlap each other in a plan view in the first direction.

In the structure described above, the gas-liquid separator, the electronic unit, and the insulating sheet overlap the communicating hole in the plan view in the first direction. Accordingly, the insulating sheet can prevent an electric current from flowing from the outside of the case to the electronic unit through the gas-liquid separator.

It is possible to prevent an electric current from flowing from the outside of the case to the electronic unit.

DESCRIPTION OF THE PREFERRED EMBODIMENTS

First Embodiment

A biological device according to a first embodiment will be described below with reference to the drawings. It should be noted that the drawings may be illustrated with components enlarged for ease of understanding. The dimensional proportions of components may differ from actual dimensional proportions or from dimensional proportions in other drawings.

Figure 1:
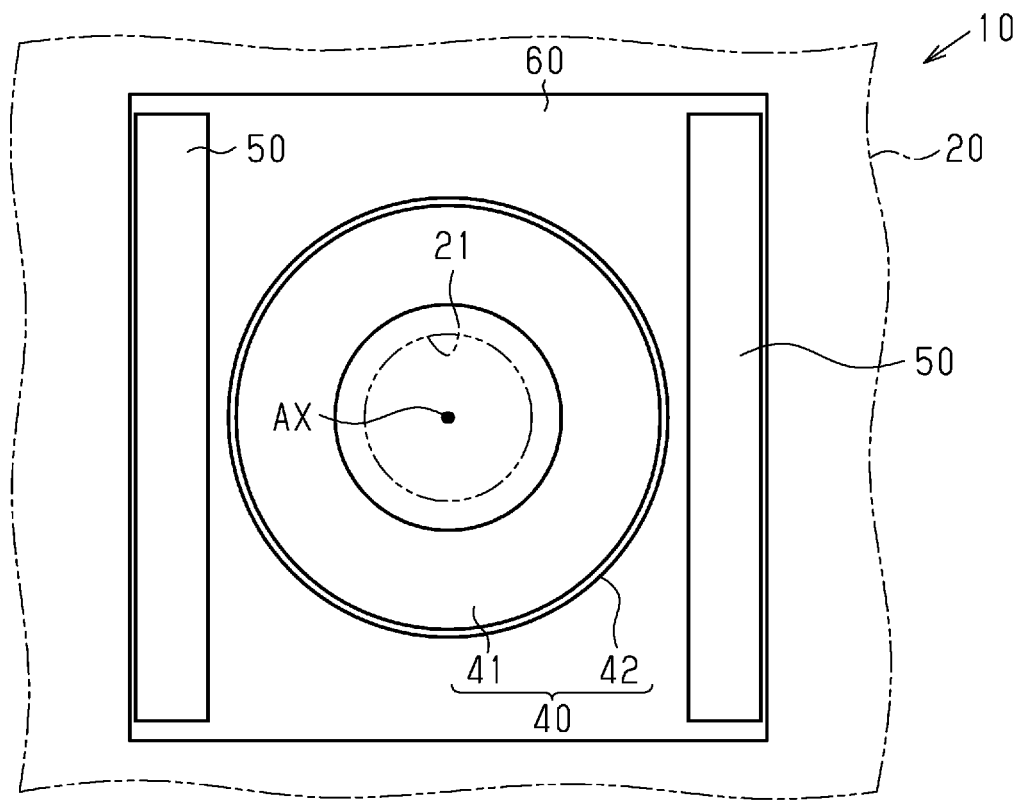
FIG. 1 is a plan view illustrating part of a biological device according to a first embodiment.
Figure 2:
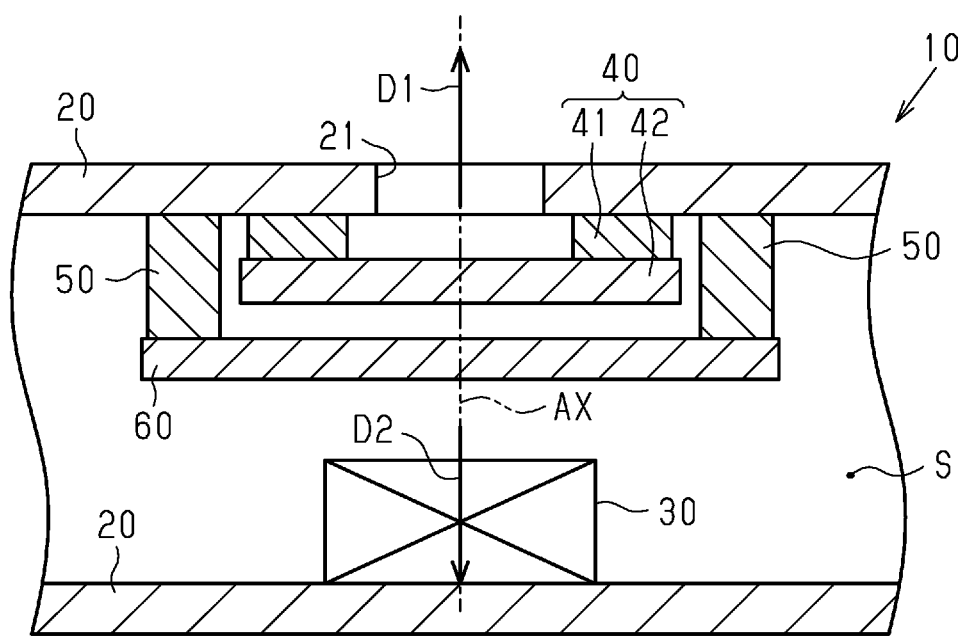
FIG. 2 is a sectional view illustrating part of the biological device according to the first embodiment.

As illustrated in FIG. 1, a biological device 10 has a case 20. The case 20 is wearable on a body. As illustrated in FIG. 2, the case 20 defines an internal space S. The material of the case 20 is, for example, a synthetic resin. Accordingly, the case 20 elastically deforms so as to follow the movement of the skin when the case 20 is pasted to the skin of a body or the like.

The case 20 has a circular communicating hole 21. The communicating hole 21 connects the internal space S and the external space of the case 20 to each other. The communicating hole 21 is a cavity present in a surface that differs from the surface of the case 20 to be pasted to the skin. Accordingly, the communicating hole 21 is not blocked by the body even when the biological device 10 is worn on the body.

It should be noted that the axis that extends in the direction of the cavity of the communicating hole 21 and passes through the center of the cavity of the communicating hole 21 is assumed to be a virtual axis AX. In addition, of the directions of the virtual axis AX, the direction from the internal space S to the external space of the case 20 is assumed to be a first direction D1. Similarly, of the directions of the virtual axis AX, the direction opposite to the first direction D1 is assumed to be a second direction D2. That is, the communicating hole 21 communicates in the first direction D1 to connect the internal space S of the case 20 and the external space of the case 20 to each other.

The biological device 10 has an electronic unit 30. The electronic unit 30 is located in the internal space S. Accordingly, the electronic unit 30 is built into the case 20. The electronic unit 30 has, for example, electronic circuits, a power supply, and electronic boards. Particularly in this embodiment, the electronic unit 30 has a temperature sensor. That is, the biological device 10 is a biological sensor that detects the temperature of a body by using the temperature sensor.

The electronic unit 30 is located at a position that overlaps the communicating hole 21 in plan view in the direction of the cavity of the communicating hole 21. Specifically, the electronic unit 30 is located on the virtual axis AX. In addition, the electronic unit 30 overlaps the entire area of the communicating hole 21 in plan view in the direction of the cavity of the communicating hole 21.

The biological device 10 has a gas-liquid separator The gas-liquid separator 40 is pervious to gas and impervious to liquid water. Specifically, the material of the gas-liquid separator 40 is polytetrafluoroethylene. In addition, the gas-liquid separator 40 has a porous structure. In this specification, imperviousness to liquid water means imperviousness to liquid water at 0.3 atmospheres. It should be noted that the water resistance of the gas-liquid separator is 200 kPa in the embodiment. Since the gas-liquid separator 40 has a porous structure in the embodiment, water passes through the gas-liquid separator 40 when an externally applied pressure exceeds the water resistance.

The gas-liquid separator 40 is attached to the case 20. The gas-liquid separator 40 blocks the communicating hole 21. Accordingly, the gas-liquid separator 40 blocks the ingress and egress of water through the communicating hole 21. Specifically, the gas-liquid separator 40 has a first spacer 41 and a gas-liquid separation sheet 42. It should be noted that the first spacer 41 and the gas-liquid separation sheet 42 are illustrated as separate components in FIG. 2, but these components may be molded as one integrated component.

As illustrated in FIG. 1, the first spacer 41 is annular. The inner diameter of the first spacer 41 is larger than the diameter of the communicating hole 21. In addition, the first spacer 41 surrounds the communicating hole 21 from the outside in plan view of the biological device 10 in the second direction D2. The first spacer 41 is attached to an inner surface of the case 20 with an adhesive, which is not illustrated.

As illustrated in FIG. 2, the gas-liquid separation sheet 42 is attached to a surface of the first spacer 41 that faces the second direction D2 with an adhesive, which is not illustrated. As illustrated in FIG. 1, the gas-liquid separation sheet 42 is circular. The diameter of the gas-liquid separation sheet 42 is larger than the diameter of the communicating hole 21. Accordingly, the area of the gas-liquid separation sheet 42 is larger than the area of the communicating hole 21 in plan view of the biological device 10 in the second direction D2. In addition, the gas-liquid separation sheet 42 overlaps the entire range of the communicating hole 21 in plan view of the biological device 10 in the second direction D2.

In the structure described above, the gas-liquid separator 40 separates the internal space S of the case 20 into the space containing the electronic unit 30 and the space not containing the electronic unit 30 with the gas-liquid separator 40 disposed therebetween as the boundary. In addition, the gas-liquid separator 40 prevents intrusion of liquid water into the space containing the electronic unit 30, which is one side of the gas-liquid separator 40, within the internal space S of the case 20 through the communicating hole 21. As described above, the gas-liquid separator 40 blocks the communicating hole 21 to prevent liquid water from flowing into the internal space S.

The biological device 10 includes two second spacers 50 and an insulating sheet 60. The second spacers 50 are present between the inner surface of the case 20 and the insulating sheet 60. The material of the second spacers 50 is, for example, polyethylene terephthalate. That is, the material of the second spacers 50 is impervious to gas. In addition, the material of the second spacers 50 is an insulator that does not conduct electricity.

The dimension in the direction of the virtual axis AX of the second spacers 50 is larger than the maximum dimension in the direction of the virtual axis AX of the gas-liquid separator 40. The two second spacers 50 are disposed on both sides of the communicating hole 21 in plan view of the biological device 10 in the second direction D2. Accordingly, the two second spacers 50 are disposed so as to sandwich the communicating hole 21 in plan view in the first direction D1. In addition, the two second spacers 50 are parallel to each other. As a result, there is a gap between the two second spacers 50. That is, the two second spacers 50 partially surround the communicating hole 21 in plan view of the biological device 10 in the second direction D2. The second spacers 50 are attached to the inner surface of the case 20 with an adhesive, which is not illustrated.

It should be noted that, when the second spacers 50 partially surround the communicating hole 21, part of the communicating hole 21 is not surrounded by the second spacers That is, in plan view of the biological device 10 in the second direction D2, when there is a passage from the communicating hole 21 to the space outside the second spacers without crossing the second spacers 50, the second spacers are said to partially surround to the communicating hole 21.

The insulating sheet 60 is attached to the surfaces of the second spacers 50 that face the second direction D2 with an adhesive, which is not illustrated. Accordingly, the insulating sheet 60 is attached to the case 20 via the second spacers 50. In addition, the insulating sheet 60 is disposed at a point away from the communicating hole 21 in the direction of the virtual axis AX. Furthermore, the insulating sheet 60 is also disposed at a position away from the gas-liquid separator 40 in the direction of the virtual axis AX. That is, the gas-liquid separator 40 and the insulating sheet are disposed away from each other in the first direction D1. As described above, in the biological device 10, the electronic unit 30, the insulating sheet 60, the gas-liquid separator 40, and the communicating hole 21 are located in this order in the first direction D1.

The material of the insulating sheet 60 is an insulator. Specifically, the material of the insulating sheet is polytetrafluoroethylene. In addition, the material of the insulating sheet 60 is impervious to gas. Specifically, unlike the gas-liquid separator 40, the insulating sheet 60 does not have a porous structure.

The insulating sheet 60 is rectangular. The dimension of one side of the insulating sheet 60 is slightly larger than the dimension in the longitudinal direction of the second spacers 50. The two sides of the insulating sheet 60 that face each other are parallel to the longitudinal direction of the second spacers 50 in plan view of the biological device 10 in the second direction D2. The insulating sheet 60 overlaps the entire range of the communicating hole 21 in plan view of the biological device 10 in the second direction D2. As described above, the gas-liquid separator 40, the electronic unit 30, and the insulating sheet 60 overlap the communicating hole 21 in plan view in the first direction D1.

In addition, the dimension of one side of the insulating sheet 60 is larger than the diameter of the communicating hole 21 in plan view of the biological device 10 in the second direction D2. Accordingly, the area of the insulating sheet 60 is larger than the area of the communicating hole 21 in plan view of the biological device 10 in the second direction D2.

Furthermore, the dimension of one side of the insulating sheet 60 is larger than the diameter of the gas-liquid separation sheet 42 in plan view of the biological device 10 in the second direction D2. Accordingly, the area of the insulating sheet 60 is larger than the area of the gas-liquid separation sheet 42 in plan view of the biological device 10 in the second direction D2.

In addition, the outer edge of the insulating sheet 60 surrounds the outer edge of the gas-liquid separator 40 in plan view of the biological device 10 in the second direction D2. That is, the area of the insulating sheet 60 is larger than the area of the gas-liquid separator 40 in plan view of the biological device 10 in the second direction D2.

Operation of the First Embodiment

The biological device 10 is used by being worn on the body. When the case 20 of the biological device 10 is pasted to the skin or the like, the case 20 deforms so as to follow the movement of the skin. Since the volume of the internal space S of the case 20 changes when the case 20 deforms, air flows between the internal space S and the external space of the case 20.

At this time, the gas-liquid separator 40 does not block the circulation of gas through the communicating hole 21 because gas passes through the gas-liquid separator 40. In addition, since the insulating sheet 60 is away from the communicating hole 21 in the direction of the virtual axis AX, the insulating sheet 60 does not block the circulation of gas through the communicating hole 21.

Effect of the First Embodiment (1-1) In the first embodiment described above, the gas-liquid separator 40, the electronic unit 30, and the insulating sheet 60 overlap the communicating hole 21 in plan view in the first direction D1. Accordingly, the insulating sheet 60 can prevent an electric current from flowing from the external space of the case 20 to the electronic unit 30 through the communicating hole 21.

(1-2) In the first embodiment described above, the insulating sheet 60 overlaps the entire range of the communicating hole 21 in plan view of the biological device 10 in the second direction D2. This can prevent an electric current from flowing from the external space of the case 20 to the electronic unit 30 through the communicating hole 21 with great certainty.

(1-3) In the first embodiment described above, the second spacers 50 partially surround the communicating hole 21. Accordingly, since air can flow through the portions in which the second spacers 50 are not provided, the second spacers 50 do not excessively prevent a flow of air between the external space and the internal space S of the case 20.

(1-4) In the first embodiment described above, the second spacers 50 are positioned so as to sandwich the communicating hole 21 in plan view in the first direction D1. This prevents the case 20 from deforming such that the gap between the second spacers 50 and the case 20 closes.

(1-5) In the first embodiment described above, the area of the insulating sheet 60 is larger than the area of the communicating hole 21 in transparent view of the biological device 10 in the second direction D2. This can extend the route of the electric current from the external space of the case 20 to the electronic unit 30 through the communicating hole 21. This can suppress the electric current from the outside of the case 20 from reaching the electronic unit 30.

(1-6) In the first embodiment described above, the area of the insulating sheet 60 is larger than the area of the gas-liquid separator 40 in transparent view of the biological device 10 in the second direction D2. Accordingly, the route from the external space of the case 20 to the electronic unit through the communicating hole 21 can be longer regardless of a portion of the gas-liquid separator 40 through which the route passes. This can further suppress the electric current from the outside of the case 20 from reaching the electronic unit 30.

(1-7) In the first embodiment described above, both the insulating sheet 60 and the gas-liquid separator 40 are disposed in the internal space S. Accordingly, when the biological device 10 is worn on the body for use, the case 20 protects the insulating sheet 60 and the gas-liquid separator 40 against physical impact from the external space of the case 20. Accordingly, the insulating sheet 60 and the gas-liquid separator 40 can be prevented from being damaged.

Second Embodiment

A biological device according to a second embodiment will be described below with reference to the drawings. It should be noted that the differences from the biological device 10 according to the first embodiment will be mainly described below, and details on the same points will be described briefly or omitted.

Figure 3:
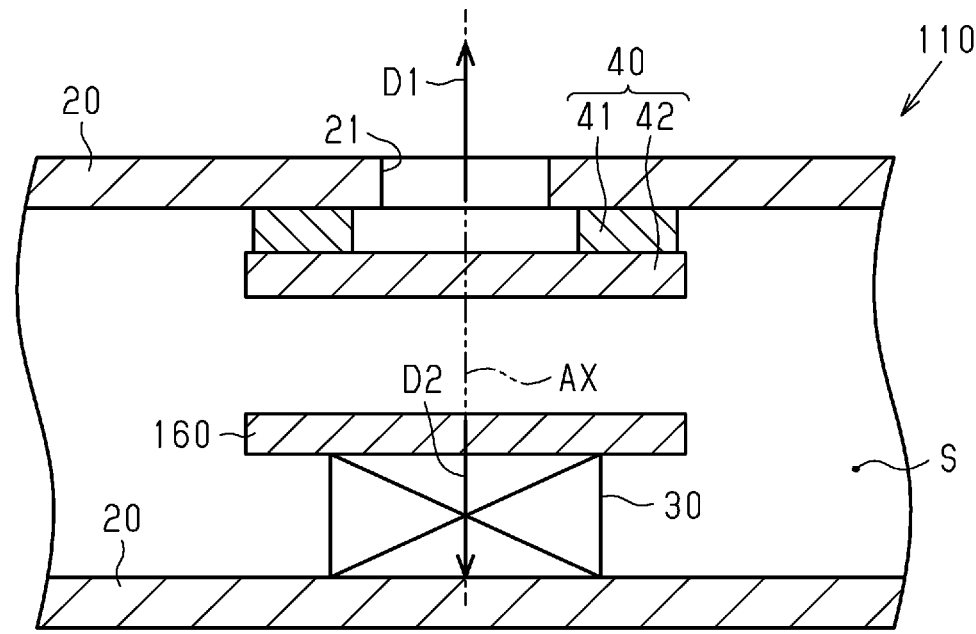
FIG. 3 is a sectional view illustrating part of a biological device according to a second embodiment.

As illustrated in FIG. 3, the second embodiment differs from the first embodiment mainly in that a biological device 110 does not have the second spacers 50 in the first embodiment and the insulating sheet 160 is disposed at a different position. The insulating sheet 160 is attached to the surface of the electronic unit 30 that faces the first direction D1.

(2-1) In the second embodiment described above, the insulating sheet 160 is attached to the electronic unit 30. Accordingly, the second spacers 50 in the first embodiment can be omitted. Also, compared with the first embodiment in which both the insulating sheet 160 and the gas-liquid separator 40 are attached to the inner surface of the case 20, the insulating sheet 160 and the gas-liquid separator 40 can be easily disposed from each other. Accordingly, the insulating sheet 160 covers the entire gas-liquid separator 40, so that the insulating sheet 160 can easily block the circulation of gas through the communicating hole 21. In addition, since the electronic unit 30 is less likely to deform than the case 20, the position of the insulating sheet 160 can be suppressed from displacing by use.

Third Embodiment

A biological device according to a third embodiment will be described below with reference to the drawings. It should be noted that the differences from the biological device 10 according to the first embodiment will be mainly described below, and details on the same points will be described briefly or omitted.

Figure 4:
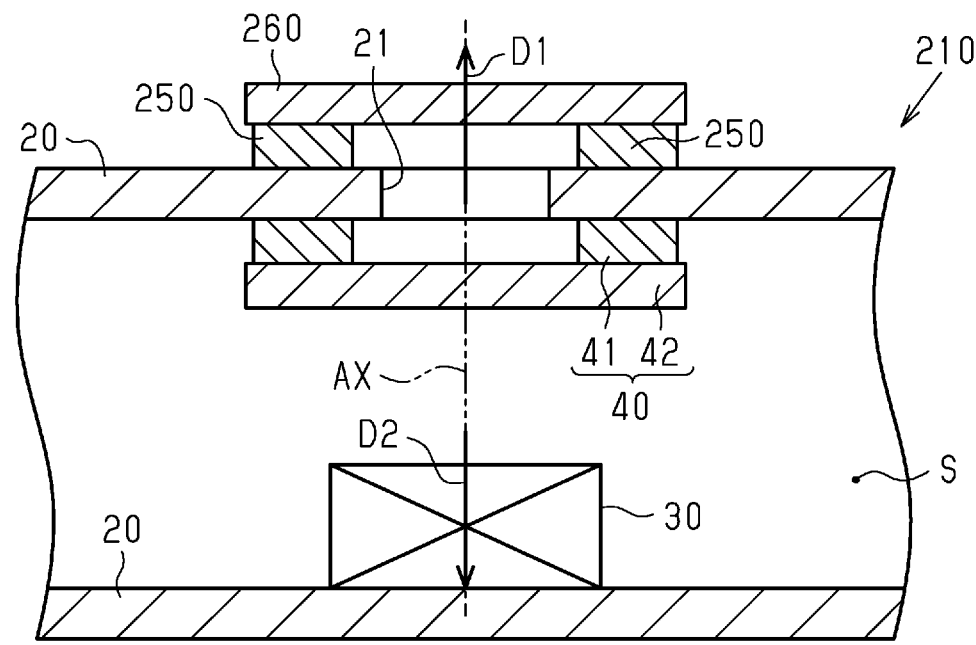
FIG. 4 is a sectional view illustrating part of a biological device according to a third embodiment.

As illustrated in FIG. 4, in the third embodiment, the positions of the second spacers 250 and the insulating sheet 260 of the biological device 210 differ from those in the first embodiment. The second spacers 250 are attached to the external surface of the case 20 with an adhesive, which is not illustrated. In addition, the gap between the two second spacers 250 is smaller than that in the first embodiment.

The insulating sheet 260 is attached to the surfaces of the second spacers 250 that face the first direction D1 with an adhesive, which is not illustrated. The area of the insulating sheet 260 is smaller than that in the first embodiment when the biological device 10 is viewed in the second direction D2. Specifically, the dimension of one side of the insulating sheet 260 is equal to the dimension of the diameter of the gas-liquid separation sheet 42.

As described above, the second spacers 250 and the insulating sheet 260 are disposed in the external space of the case 20. Accordingly, the electronic unit 30, the gas-liquid separator 40, the communicating hole 21, and the insulating sheet 260 are located in this order in the first direction D1.

(3-1) In the third embodiment described above, the insulating sheet 260 can be attached to the external surface of the case 20 via the second spacers 250. Accordingly, unlike the first embodiment, when the insulating sheet 260 is attached to the case 20, the position of the gas-liquid separator 40 need not be considered. Accordingly, the insulating sheet 260 can be attached to the case 20 more easily.

Fourth Embodiment

A biological device according to the fourth embodiment will be described with reference to the drawings. It should be noted that the differences from the biological device 210 according to the third embodiment will be mainly described below, and details on the same points will be described briefly or omitted.

Figure 5:
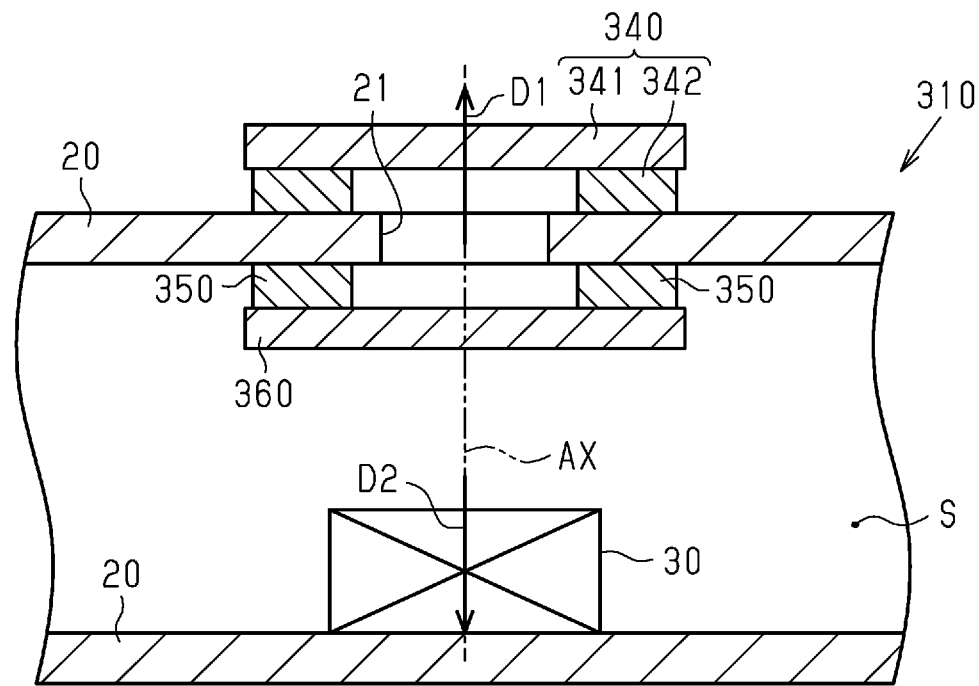
FIG. 5 is a sectional view illustrating part of a biological device according to a fourth embodiment.

As illustrated in FIG. 5, the positions of the second spacers 350 and the insulating sheet 360 of the biological device 310 and the position of the gas-liquid separator 340 in the fourth embodiment are exchanged with those in the third embodiment.

Specifically, the first spacer 341 of the gas-liquid separator 340 is attached to the external surface of the case 20 with an adhesive, which is not illustrated. In addition, the gas-liquid separator 342 is attached to the surface of the first spacers 341 that face the first direction D1 with an adhesive, which is not illustrated.

The second spacers 350 are attached to the inner surface of the case 20 with an adhesive, which is not illustrated. In addition, the insulating sheet 360 is attached to the surfaces of the second spacers 350 that face the second direction D2 with an adhesive, which is not illustrated.

In this way, the gas-liquid separator 340 is disposed in the external space of the case 20. On the other hand, the second spacers 350 and the insulating sheet 360 are disposed in the internal space S of the case 20. Accordingly, the electronic unit 30, the insulating sheet 360, the communicating hole 21, and the gas-liquid separator 340 are located in this order in the first direction D1.

(4-1) In the fourth embodiment described above, the gas-liquid separator 340 can be attached to the outer surface of the case 20. Accordingly, unlike the first embodiment, when the gas-liquid separator 340 is attached to the case 20, the position of the insulating sheet 360 need not be considered. Accordingly, the insulating sheet 360 can be attached to the case 20 more easily.

Fifth Embodiment

A fifth embodiment of the biological device will be described below with reference to the drawings. It should be noted that the differences from the biological device 10 according to the first embodiment will be mainly described below, and details on the same points will be described briefly or omitted.

Figure 6:
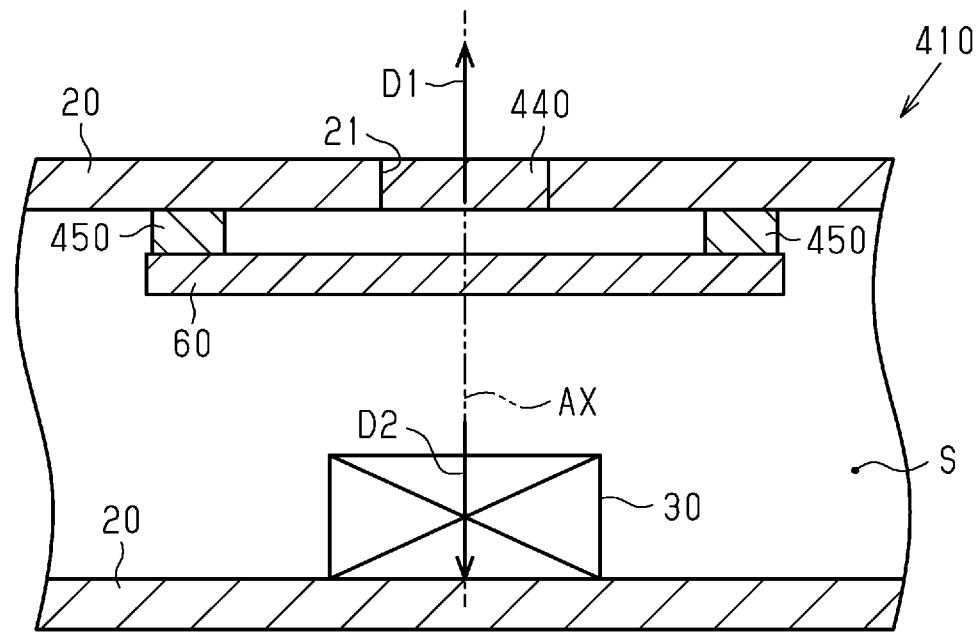
FIG. 6 is a sectional view illustrating part of a biological device according to a fifth embodiment.

As illustrated in FIG. 6, in the fifth embodiment, the position of the gas-liquid separator 440 of the biological device 410 differs from that in the first embodiment. Specifically, the gas-liquid separator 440 is housed in the communicating hole 21. Particularly in the embodiment, the communicating hole 21 is completely filled with the gas-liquid separator 440. Accordingly, the gas-liquid separator 440 blocks the communicating hole 21. Furthermore, the gas-liquid separator 440 is present only within the communicating hole 21. That is, the gas-liquid separator 440 does not protrude outside the communicating hole 21. Accordingly, in the fifth embodiment, it can be said that the case 20 does not have the communicating hole 21. In addition, part of the wall of the case 20 is formed by the gas-liquid separator 440. It should be noted that, in the fifth embodiment, gas can pass between the internal space S of the case 20 and the external space of the case 20 through the gas-liquid separator 440 in the thickness direction of the wall of the case 20. Accordingly, the thickness direction of the portion of the wall of the case 20 formed by the gas-liquid separator 440 is aligned with the virtual axis AX.

As described above, the communicating hole 21 and the gas-liquid separator 440 are located at the same position in the direction of the virtual axis AX. In addition, the electronic unit 30, the insulating sheet 60, and the communicating hole 21 are located in this order in the first direction D1.

It should be noted that the dimension in the direction of the virtual axis AX of the second spacers 450 of the biological device 410 is smaller than that in the first embodiment.

(5-1) In the fifth embodiment described above, the space inside the communicating hole 21 can be used to dispose the gas-liquid separator 440. Accordingly, the internal space S need not be excessively large to provide the gas-liquid separator 440. As a result, the enlargement of the biological device 410 is more likely to be suppressed.

(5-2) In the fifth embodiment described above, the insulating sheet 60 is disposed in the internal space S. Accordingly, when the biological device 410 is used by being attached to the body, the insulating sheet 60 is protected by the case 20.

OTHER EMBODIMENTS

The embodiments described above can be implemented by being changed as described below. The embodiments described above and the following modifications can be implemented in combination without technical inconsistencies.

The biological device is not limited to a biological sensor as long as the device is worn on a body. That is, the electronic unit 30 may have no sensors.

It should be noted that, when the biological device is a biological sensor, for example, a discharging device, such as a cautery knife or a defibrillator, are used near a portion of the body on which the biological device is worn with the biological device attached to the body, an electric current is likely to flow into the sensor from the outside of the case 20.

Accordingly, there is a greater need to obtain the benefits of providing the insulating sheet.

The case 20 may be a film. That is, the case 20 need only have the rigidity for maintaining its own shape. In this case, the virtual axis AX with the case 20 worn on the body need only be used as the reference.

The material of the gas-liquid separator is not limited to polytetrafluoroethylene. The material of the gas-liquid separator need only be pervious to gas and impervious to liquid water. The water resistance of the gas-liquid separator need only be 30 kPa or more.

The shape of the gas-liquid separator may be changed as appropriate as long as the communicating hole 21 is blocked. For example, in the first embodiment, the gas-liquid separator 40 may be block-shaped. It should be noted that, as in the fifth embodiment, the communicating hole 21 may be absent in the case 20 because the gas-liquid separator 440 blocks the communicating hole 21.

In the first to the fourth embodiments, the gas-liquid separator need not have the first spacer as in the fifth embodiment. For example, in the first embodiment, the gas-liquid separation sheet 42 may be attached to the inner surface of the case 20 without the first spacer 41.

The shape of the second spacers is not limited to the examples in the embodiments described above. For example, in the first embodiment, the second spacers 50 may be C-shaped or spiral-shaped in transparent view of the biological device 10 in the second direction D2. In these cases, the second spacers 50 partially surround the communicating hole 21 in transparent view of the biological device 10 in the second direction D2.

In the first embodiment and the third to fifth embodiments, the second spacers may surround the entire communicating hole 21 in transparent view of the biological device in the second direction D2. In this case, in the first embodiment, for example, a partial gap need only be present between the insulating sheet 60 and the second spacers 50, or the material of the second spacers 50 need only be a material that is pervious to gas. As described above, the circulation of gas between the space inside the second spacers 50 and the space outside the second spacers 50 need not only be blocked in transparent view of the biological device 10 in the second direction D2.

The material of the second spacers need not be an insulator.

In the third embodiment, the biological device 210 need not have the second spacers 250. This also applies to the fourth embodiment and the fifth embodiment.

The area of the insulating sheet is not limited to the examples of the embodiments described above in transparent view of the biological device in the second direction D2. For example, in the first embodiment, the area of the insulating sheet 60 may be equal to the area of the communicating hole 21 in transparent view of the biological device 10 in the second direction D2. Alternatively, for example, in the first embodiment, the area of the insulating sheet 60 may be equal to or less than the area of the gas-liquid separator 40 in transparent view of the biological device 10 in the second direction D2.

In the embodiments, the order in the first direction D1 of the electronic unit 30, the insulating sheet, the gas-liquid separator, and the communicating hole 21 may be changed by changing the disposition of these components. The gas-liquid separator, the electronic unit 30, and the insulating sheet need only overlap the communicating hole 21 in plan view in the first direction facing D1. As a result, for example, the insulating sheet 60 and the gas-liquid separator 40 may be disposed in the external space of the case 20 in the first embodiment.

Technical concepts that can be grasped from the embodiments and the modifications described above are as follows:

<1> A biological device that includes: a case defining an internal space and having a communicating hole connecting the internal space and an external space of the case to each other along a first direction, the case being constructed to be wearable on a body; an electronic unit in the internal space of the case; a gas-liquid separator attached to the case and blocking the communication hole; and an insulating sheet attached to the case or the electronic unit and disposed apart from the gas-liquid separator in the first direction, wherein the gas-liquid separator, the electronic unit, and the insulating sheet overlap the communicating hole in a plan view of the biological device in the first direction.

<2> The biological device according to <1>, wherein the insulating sheet is attached to the case, and the biological device further comprises: a spacer between the case and the insulating sheet, wherein the spacer is arranged to sandwich the communicating hole in the plan view in the first direction.

<3> The biological device according to <1> or <2>, wherein an area of the insulating sheet is larger than an area of the communicating hole in the plan view in the first direction.

<4> The biological device according to any one of <1> to <3>, wherein an area of the insulating sheet is larger than an area of the gas-liquid separator in the plan view in the first direction.

<5> The biological device according to any one of <1> to <4>, wherein, when the first direction extends in a direction from the internal space to the external space of the case, the electronic unit, the insulating sheet, the gas-liquid separator, and the communicating hole are arranged in this order in the first direction.

<6> The biological device according to any one of <1> to <4>, wherein, when the first direction extends in a direction from the internal space to the external space of the case, the electronic unit, the insulating sheet, the communicating hole, and the gas-liquid separator are arranged in this order in the first direction.

<7> The biological device according to any one of <1> to <4>, wherein, when the first direction extends in a direction from the internal space to the external space of the case among directions in which the communicating hole extends, the electronic unit, the insulating sheet, the communicating hole, and the gas-liquid separator are arranged in this order in the first direction.

<8> A biological device that includes: a case wearable on a body; a gas-liquid separator constituting part of a wall of the case, the gas-liquid separator forming a path allowing gas to pass between an internal space within the case and an external space of the wall in a first direction, the first direction being a thickness direction of the wall; an electronic unit in the case; and an insulating sheet attached to the case or the electronic unit and disposed apart from the gas-liquid separator in the first direction, wherein the gas-liquid separator, the electronic unit, and the insulating sheet overlap each other in a plan view in the first direction.

<9> The biological device according to <8>, wherein, when the first direction extends in a direction from the internal space to the external space of the case, the electronic unit, the insulating sheet, and the gas-liquid separator are arranged in this order in the first direction.

What is claimed is:

1. A biological device comprising:
   a case defining an internal space and having a communicating hole connecting the internal space and an external space of the case to each other along a first direction, the case being constructed to be wearable on a body;
   an electronic unit in the internal space of the case;
   a gas-liquid separator attached to the case and blocking the communication hole; and
   an insulating sheet attached to the case or the electronic unit and disposed apart from the gas-liquid separator in the first direction,
   wherein the gas-liquid separator, the electronic unit, and the insulating sheet overlap the communicating hole in a plan view of the biological device in the first direction.

2. The biological device according to claim 1, wherein the insulating sheet is attached to the case, and the biological device further comprises:
   a spacer between the case and the insulating sheet,
   wherein the spacer is arranged to sandwich the communicating hole in the plan view in the first direction.

3. The biological device according to claim 1, wherein the insulating sheet is attached to the electronic unit.

4. The biological device according to claim 1, wherein an area of the insulating sheet is larger than an area of the communicating hole in the plan view in the first direction.

5. The biological device according to claim 4, wherein the area of the insulating sheet is larger than an area of the gas-liquid separator in the plan view in the first direction.

6. The biological device according to claim 1, wherein an area of the insulating sheet is larger than an area of the gas-liquid separator in the plan view in the first direction.

7. The biological device according to claim 1, wherein, when the first direction extends in a direction from the internal space to the external space of the case, the electronic unit, the insulating sheet, the gas-liquid separator, and the communicating hole are arranged in this order in the first direction.

8. The biological device according to claim 1, wherein, when the first direction extends in a direction from the internal space to the external space of the case, the electronic unit, the gas-liquid separator, the communicating hole, and the insulating sheet are arranged in this order in the first direction.

9. The biological device according to claim 1, wherein, when the first direction extends in a direction from the internal space to the external space of the case, the electronic unit, the insulating sheet, the communicating hole, and the gas-liquid separator are arranged in this order in the first direction.

10. The biological device according to claim 1, wherein the gas-liquid separating sheet is arranged in the communication hole.

11. A biological device comprising:
    a case wearable on a body;
    a gas-liquid separator constituting part of a wall of the case, the gas-liquid separator forming a path allowing gas to pass between an internal space within the case and an external space of the wall in a first direction, the first direction being a thickness direction of the wall;
    an electronic unit in the case; and
    an insulating sheet attached to the case or the electronic unit and disposed apart from the gas-liquid separator in the first direction,
    wherein the gas-liquid separator, the electronic unit, and the insulating sheet overlap each other in a plan view in the first direction.

12. The biological device according to claim 11, wherein, when the first direction extends in a direction from the internal space to the external space of the case, the electronic unit, the insulating sheet, and the gas-liquid separator are arranged in this order in the first direction.

13. The biological device according to claim 11, further comprising a spacer between the case and the insulating sheet, the spacer attaching the insulating sheet to the case.

14. The biological device according to claim 11, wherein the area of the insulating sheet is larger than an area of the gas-liquid separator in the plan view in the first direction.

* * * * *